(12) United States Patent
Ware et al.

(10) Patent No.: US 9,302,092 B2
(45) Date of Patent: Apr. 5, 2016

(54) MULTI-FUNCTION LEAD IMPLANT TOOL

(75) Inventors: Eric A. Ware, Plymouth, MN (US); G. Shantanu Reddy, Minneapolis, MN (US); Bradley Woodcox, Butler, IN (US); Robbie Halvorson, Santa Clara, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1374 days.

(21) Appl. No.: 12/976,562

(22) Filed: Dec. 22, 2010

(65) Prior Publication Data
US 2011/0160824 A1 Jun. 30, 2011

Related U.S. Application Data

(60) Provisional application No. 61/291,163, filed on Dec. 30, 2009.

(51) Int. Cl.
*A61N 1/05* (2006.01)
*H01R 24/58* (2011.01)
(Continued)

(52) U.S. Cl.
CPC .... *A61N 1/05* (2013.01); *H01R 24/58* (2013.01); *H01R 11/24* (2013.01); *H01R 31/06* (2013.01); *H01R 2103/00* (2013.01); *H01R 2201/12* (2013.01)

(58) Field of Classification Search
CPC ....... A61N 1/05; A61N 1/056; A61N 1/0563; A61N 1/0257; A61N 1/0573; A61N 1/059; A61N 1/3956; A61N 1/3752; H01R 24/58; H01R 2201/12; H01R 2103/00; H01R 31/06; H01R 11/24; H01R 11/22; H01R 27/00

USPC ........ 606/129; 607/126, 122, 5, 9, 27, 15, 28, 607/119, 37, 38, 116; 600/377, 373, 374, 600/394; 439/909, 470, 574, 575, 593, 725, 439/726, 769, 772, 806, 822, 833
See application file for complete search history.

(56) References Cited

U.S. PATENT DOCUMENTS 4,027,678 A * 6/1977 van Oostveen et al. ......... 607/37
4,209,019 A   6/1980 Dutcher et al.
(Continued)

FOREIGN PATENT DOCUMENTS

WO   WO0056402 A1   9/2000
WO   WO2004101068 A1   11/2004

OTHER PUBLICATIONS

International Search Report and Written Opinion issued in PCT/US2010/062215, mailed Jan. 31, 2012.

*Primary Examiner* — Jocelin Tanner
(74) *Attorney, Agent, or Firm* — Faegre Baker Daniels LLP

(57) ABSTRACT

Devices, systems, and methods for implanting and testing multi-conductor electrical leads are disclosed. An illustrative implant tool for use with an implantable lead includes a main body, a plurality of spring contact members, and a knob mechanism. The main body of the implant tool includes a distal clamping mechanism with an opening adapted to frictionally receive a terminal boot of the implantable lead. The spring contact members are configured to provide an interface for connecting electrical connectors from a Pacing System Analyzer (PSA) or other testing device to the terminal contacts on the implantable lead. A knob mechanism coupled to the main body can be actuated to engage a terminal pin of the implantable lead, allowing an implanting physician to engage a fixation helix into body tissue by rotating the mechanism.

19 Claims, 10 Drawing Sheets

(51) Int. Cl.
   *H01R 11/24* (2006.01)
   *H01R 31/06* (2006.01)
   *H01R 103/00* (2006.01)

(56) References Cited

U.S. PATENT DOCUMENTS

| | | | |
|---|---|---|---|
| 4,278,093 A * | 7/1981 | Lafortune et al. | 607/37 |
| 4,744,371 A | 5/1988 | Harris | |
| 5,275,620 A | 1/1994 | Darby et al. | |
| 5,334,045 A | 8/1994 | Cappa et al. | |
| 5,354,326 A | 10/1994 | Comben et al. | |
| 5,535,745 A | 7/1996 | Ingram et al. | |
| 5,557,210 A | 9/1996 | Cappa et al. | |
| 5,679,022 A | 10/1997 | Cappa et al. | |
| 5,782,841 A | 7/1998 | Ritz et al. | |
| 5,782,892 A | 7/1998 | Castle et al. | |
| 5,931,861 A | 8/1999 | Werner et al. | |
| 6,038,479 A | 3/2000 | Werner et al. | |
| 6,038,481 A | 3/2000 | Werner et al. | |
| 6,129,751 A * | 10/2000 | Lucchesi et al. | 607/127 |
| 6,162,101 A | 12/2000 | Fischer et al. | |
| 6,192,278 B1 | 2/2001 | Werner et al. | |
| 6,343,233 B1 | 1/2002 | Werner et al. | |
| 6,415,168 B1 | 7/2002 | Putz | |
| 6,463,334 B1 | 10/2002 | Flynn et al. | |
| 6,580,948 B2 | 6/2003 | Haupert et al. | |
| 6,907,292 B1 * | 6/2005 | Hill | 607/37 |
| 7,130,699 B2 | 10/2006 | Huff et al. | |
| 2003/0018364 A1 * | 1/2003 | Belden et al. | 607/37 |
| 2003/0123027 A1 | 7/2003 | Amir et al. | |
| 2004/0215302 A1 | 10/2004 | Sage et al. | |
| 2005/0177199 A1 | 8/2005 | Hansen et al. | |
| 2006/0258193 A1 * | 11/2006 | Hoecke et al. | 439/92 |
| 2008/0015668 A1 | 1/2008 | Soukup | |
| 2008/0248696 A1 | 10/2008 | Kast et al. | |
| 2008/0255630 A1 | 10/2008 | Arisso et al. | |
| 2008/0294030 A1 * | 11/2008 | von Malmborg et al. | 600/374 |

* cited by examiner

MULTI-FUNCTION LEAD IMPLANT TOOL

CROSS-REFERENCE TO RELATED APPLICATION

This application claims priority under 35 U.S.C. §119 to U.S. Provisional Application No. 61/291,163, filed on Dec. 30, 2009, entitled "Multi-Function Lead Implant Tool," which is incorporated herein by reference in its entirety for all purposes.

TECHNICAL FIELD

The present invention relates generally to implantable medical devices. More specifically, the present invention relates to devices, systems, and methods for installing and testing multi-conductor electrical leads within a patient's body.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include a distal conductor end, which contacts the heart tissue, and a proximal terminal end, which is connected to the pulse generator. The conductor end of the lead typically includes one or more features such as an active fixation helix or a number of passive tines to facilitate securing the lead to the heart tissue. The terminal end of the lead, in turn, includes one or more electrical contacts that are electrically connected to the electrodes on the terminal end of the lead via a number of conductors.

In certain applications, the leads are tested for proper positioning and function as part of the implantation process and prior to being connected to the pulse generator, allowing the implanting physician to evaluate pacing and sensing performance prior to concluding that the particular lead position is suitable. During the testing process, for example, a Pacing System Analyzer (PSA) may be connected to the terminal end of the lead to test the connection of the conductor end of the lead to the heart and/or to evaluate the performance of the lead. To facilitate connection of the PSA to the lead, a lead implant tool can be temporarily coupled to the terminal end of the lead, allowing the conductors of the PSA to be connected to the electrical contacts on the terminal end of the lead. In some cases, for example, the implant tool may facilitate the attachment of several alligator clips, plunger clips, or other spring-loaded clips to the electrical contacts on the terminal end of the lead. Examples of lead implant tools for use in connecting the conductors of a PSA to a multi-conductor lead are described in U.S. Patent Publication No. 2005/0177199 to Hansen et al. and U.S. Patent Publication No. 2006/0258193 to Hoecke et al., each of which are incorporated herein by reference in their entirety for all purposes.

More recent trends in lead designs have focused on the development of lead connectors with up to four electrical contacts. The terminal end of such leads are not significantly different in size from previous, IS-1 standard leads, which include only two terminal contacts. Many existing spring-loaded clips used for connecting the PSA to the terminal contacts are often inadequate for use with more modern lead designs, particularly due to the limited spacing between the contacts, and since the space between the contacts is sometimes used as a sealing area to ensure electrical isolation.

SUMMARY

The present invention relates generally to devices, systems, and methods for implanting and testing multi-conductor electrical leads within a body.

In Example 1, an illustrative implant tool for use with an implantable lead includes a main body, a plurality of spring contact clips, and a knob mechanism. The main body of the implant tool includes a distal clamping mechanism with an opening adapted to frictionally receive a terminal boot of the implantable lead. The spring contact clips are configured to provide an interface for connecting electrical connectors from a Pacing System Analyzer (PSA) or other testing device to the terminal contacts on the implantable lead. A knob mechanism coupled to the main body can be actuated to selectively engage or disengage a terminal pin of the implantable lead, allowing an implanting physician to engage a fixation helix by rotating the mechanism. In some embodiments, the knob can also be configured to accept a stylet wire or guidewire, and includes a funnel shape to ease stylet or guidewire orientation within the opening at the end of the terminal pin. The implant tool can be provided as part of a system including the implantable lead and a stylet or guidewire. In use, the implant tool protects the lead connector during implantation and testing of the lead.

In Example 2, the implant tool according to Example 1, wherein the main body further includes a number of levers configured to adjust the size of the opening for creating a friction-fit between the main body and the terminal end of the implantable lead.

In Example 3, the implant tool according to either Example 1 or 2, wherein the distal clamping section of the main body includes a slot and a number of indicator arrows for confirming the positioning of the terminal boot within the implant tool.

In Example 4, the implant tool according to any of Examples 1-3, wherein the knob mechanism includes a collet coupled to a knob.

In Example 5, the implant tool according to either Example 4, wherein the knob includes a funneled opening configured for receiving a stiffening member.

In Example 6, the implant tool according to Example 5, wherein the knob opening includes a wiper blade and a lubrication device.

In Example 7, the implant tool according to any of Examples 4-6, wherein the collet includes a collet body having a first section secured to an interior portion of the knob and a second section configured to engage a clutch mechanism of the main body.

In Example 8, the implant tool according to Example 7, wherein the collet body includes a gripping sleeve configured to frictionally receive the terminal pin in said first position.

In Example 9, the implant tool according to either Example 7 or 8, wherein the collet body includes a flared distal opening configured to receive a proximal end of the terminal pin in said second position.

In Example 10, the implant tool according to any of Examples 7-9, wherein the knob mechanism further includes a self-braking mechanism configured for eliminating recoil of the knob during rotation of the knob mechanism.

In Example 11, the implant tool according to any of Examples 1-10, wherein each spring contact member includes a clip having an exterior facing surface configured to receive an electrical connector and an interior facing surface configured to engage an electrical contact on the terminal end of the implantable lead.

In Example 12, the implant tool according to any of Examples 1-11, wherein the plurality of spring contact members are aligned laterally from each other along a length of the implant tool.

In Example 13, the implant tool according to any of Examples 1-12, wherein the plurality of spring contact members includes a first spring contact clip configured to engage the terminal pin of the implantable lead, and a second spring contact clip configured to engage a ring contact of the implantable lead.

In Example 14, the implant tool according to Example 13, further comprising at least one additional spring contact clip configured to engage a contact of the implantable lead.

In Example 15, the implant tool according to any of Examples 1-14, wherein each spring contact member includes a body having a first end bendable relative to a second end.

In Example 16, a system for implanting and testing an implantable lead within the body of a patient comprises an implantable lead and an implant tool. The implant tool comprises a main body having a distal clamping section, a proximal section, and an interior lumen, the distal clamping section including an opening adapted to frictionally receive a terminal boot of the implantable lead. The implant tool further includes a plurality of spring contact members coupled to the main body. A knob mechanism coupled to the main body is actuatable between a first position configured to frictionally engage a terminal pin of the implantable lead and a second position configured to disengage from the terminal pin.

In Example 17, a method for using an implant tool for implanting and testing an implantable lead within a body comprises coupling an implant tool to a terminal end of an implantable lead, the implant tool including a main body having a distal clamping section, a proximal section, and an interior lumen, the distal clamping section including an opening adapted to frictionally receive a terminal boot of the implantable lead. The implant tool further includes a plurality of spring contact members coupled to the main body. A knob mechanism coupled to the main body is actuatable between a first position configured to frictionally engage a terminal pin of the implantable lead and a second position configured to disengage from the terminal pin. The method further includes implanting the lead at a location within the body, actuating the knob mechanism to the first position and rotating the knob one or more turns to rotatably engage the terminal pin, actuating the knob mechanism to the second position to relieve any torque applied to the implantable lead during rotation of the knob, and removing the implant tool from the implantable lead.

In Example 18, the method according to Example 17, wherein coupling the implant tool to the terminal end of the implantable lead includes depressing a number of levers on the main body, inserting the terminal end of the implantable lead into the opening, and aligning the terminal end of the implantable lead within the implant tool.

In Example 19, the method according to any of Example 16-18, wherein the knob includes an opening, a wiper blade, and a lubrication device, and wherein the wiper blade and lubrication device is configured to contact and clean the stiffening member when inserted into the knob opening.

In Example 20, the method according to any of Examples 16-19, further including connecting a number of electrical connectors of a testing device to the spring contact members, and testing the implantable lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
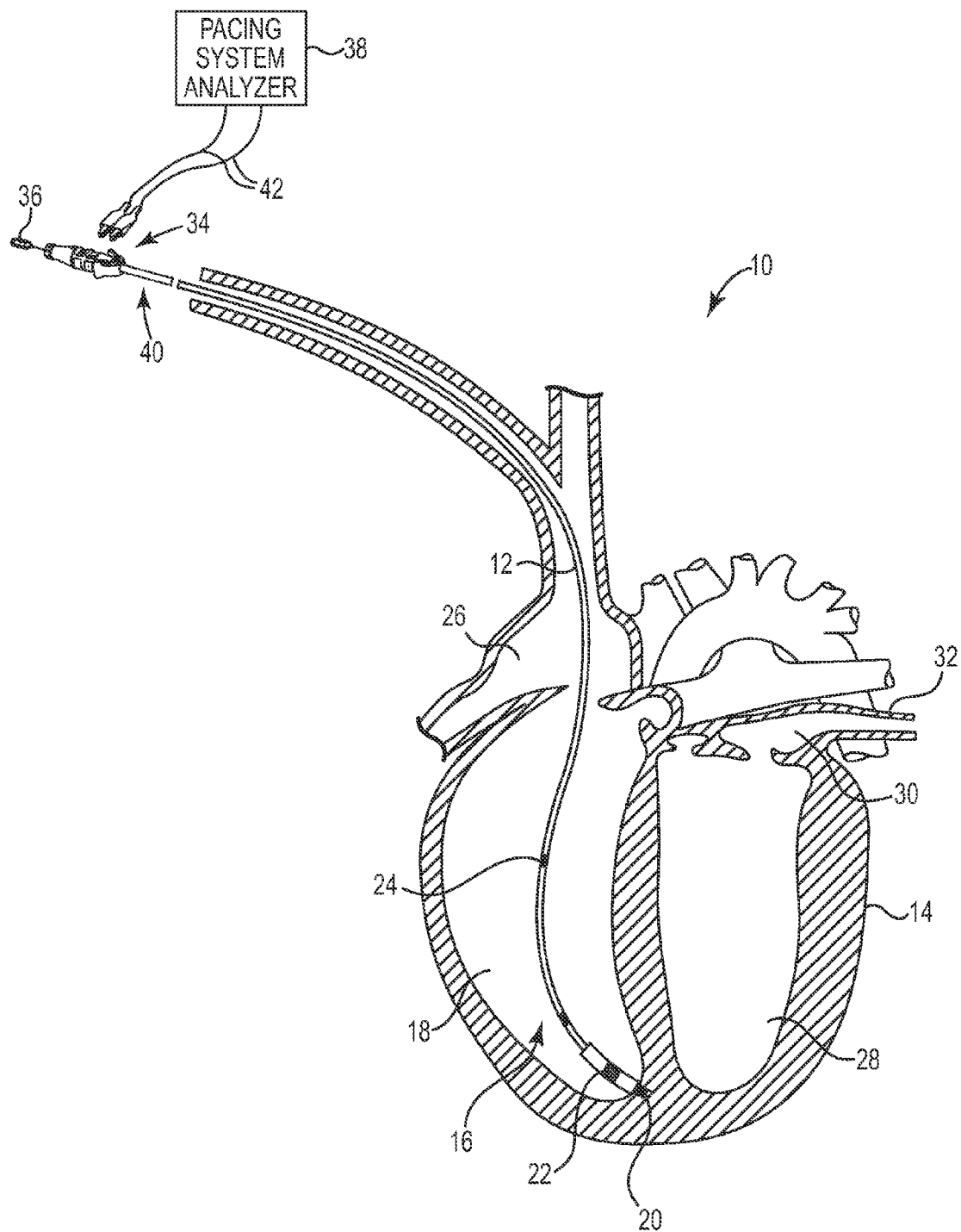
FIG. 1 is a schematic view showing an illustrative system for implanting and testing an implantable lead within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view showing an illustrative system 10 for implanting and testing an implantable lead 12 within the body of a patient. For purposes of illustration and not limitation, the system 10 is described in conjunction with an implantable lead 12 for use in sensing cardiac electrical activity and/or for providing electrical stimulus therapy to a patient's heart 14. The system 10 can be used in other contexts where implantable leads are employed, and where testing is to be conducted prior to the connection of the lead to another implantable device such as a pulse generator. In certain embodiments, for example, the system 10 can be used to aid in the implantation and testing of an implantable neurostimulation lead prior to its connection to another implantable device such as a pulse generator.

A distal, conductive end 16 of the implantable lead 12 may be located as desired by an implanting physician within, on, or about the heart 14 of a patient. In the embodiment of FIG. 1, the conductive end 16 of the lead 12 is located in an apex of the right ventricle 18, as shown. The conductive end 16 of the lead 12 includes one or more electrodes, including a distal tip electrode 20 that serves as a fixation helix and one or more ring electrodes 22. The tip and ring electrodes 20,22 are each coupled to a corresponding conductor within the lead 12, which during operation transmit electrical pulses back and forth between an implantable pulse generator (not shown) and the heart 14 for sensing cardiac activity and/or for providing pacing therapy to the heart 14. In certain embodiments, and as further shown in FIG. 1, the implantable lead 12 comprises a quadripolar lead that further includes a shocking coil 24 or multiple shocking coils 24 for providing shock therapy to the heart 14. The type of pulse generator employed will vary based on the therapy to be performed. An example pulse generator can include a pacemaker, an implantable cardioverter defibrillator (ICD), a cardiac resynchronization therapy (CRT) device, or the like.

Although the illustrative embodiment depicts only a single implantable lead 12 inserted into the patient's heart 14, in other embodiments multiple leads can be utilized so as to electrically stimulate other areas of the heart 14. In some embodiments, for example, the distal section of a second lead (not shown) may be implanted in the right atrium 26. In addition, or in lieu, another lead may be implanted in or near the left side of the heart 14 (e.g., in the left ventricle 28, the left atrium 30, or in the coronary veins 32) to stimulate the left side of the heart 14. Other types of leads such as epicardial leads may also be utilized in addition to, or in lieu of, the lead 12 depicted in FIG. 1.

In the illustrative embodiment depicted, the system 10 further includes an implant tool 34, a stiffening member such as a stylet or guidewire 36, and a Pacing System Analyzer (PSA) 38 that can be used for implanting and testing the lead 12 within the body. During the course of the procedure, to evaluate the viability of a potential fixation site, the function and location of the lead 12 can be tested by connecting a proximal, terminal end 40 of the lead 12 to several electrical conductors 42 of the PSA 38. This evaluation can be performed prior to deploying the fixation helix 20 in the case of an active fixation lead, and is then typically performed again after deploying the helix 20. Such testing can be performed, for example, to verify that one or more contacts at the terminal end 40 of the lead 12 are in electrical contact with the tip and ring electrodes 20,22, and that the electrodes 20,22 are properly positioned on or within the heart 14. The PSA 38 can also be used to perform other functions, such as programming the implantable device (e.g., pulse generator) to be coupled to the implantable lead 12, and to generate any pacing pulses necessary to support the patient during the implantation process.

The implant tool 34 is configured to permit the implanting physician to easily feed various stylets 36 into a pin lumen of the implantable lead 12. The implant tool 34 is also configured to permit the implanting physician to make an electrical connection between the PSA conductors 42 and a terminal pin 44 (shown in FIG. 2) and one or more terminal rings on the lead 12. In some embodiments, the implant tool 34 may also be used with passive fixation leads to enable stylet passage and electrical connection while protecting the terminal connector.

In some embodiments, the implant tool 34 may be used to extend and/or retract the fixation helix 20 by attaching to the terminal pin 44 which, in turn, is connected to an internal driveshaft that connects to a fixation helix deployment mechanism. The driveshaft may or may not be electrically conductive, and the fixation helix 20 may or may not be electrically active. In some embodiments, the implant tool 34 is not used for deploying a fixation mechanism. Moreover, other fixation mechanisms other than helical electrodes can also be deployed via the implant tool 34.

In some embodiments, the implant tool 34, stylet 36, and/or other components of the system 10 can be shipped as part of a kit already attached to an implantable lead 12. In certain embodiments, for example, the implant tool 34 can be pre-loaded onto a portion of the implantable lead 12 with the stylet 36 pre-inserted through the implant tool 34 and a portion of the lead 12. The pre-assembled components can then be packaged in a blister pack, pouch, or other suitable storage medium for later use by the implanting physician.

In use, the implant tool 34 protects the lead connector throughout the implant procedure from electrical clips or other surgical implements. As such, the implant tool 34 is typically removed only after the connection of the device to another implantable device such as a pulse generator is to occur. At that time, the lead implant tool 34 is removed from the lead 12, and the lead 12 is then connected to the pulse generator. During normal operation, the lead 12 is configured to convey electrical signals back and forth between the pulse generator and the heart 14. For example, in those embodiments where the pulse generator is a pacemaker, the lead 12 can be used to deliver electrical therapeutic stimulus for pacing the heart 14. In those embodiments where the pulse generator is an implantable cardioverter defibrillator (ICD), the lead 12 can be utilized to deliver electric shocks to the heart 14 in response to an event such as a heart attack or ventricular tachycardia. In some embodiments, the pulse generator includes both pacing and defibrillation capabilities, or is capable of performing biventricular or other multi-site resynchronization therapies such as cardiac resynchronization therapy (CRT). Example leads and lead connectors that can be used in conjunction with the implant tool 34 can include, but are not limited to, ICD leads (e.g., including a quadripolar, IS-1/DF-1 type connector), pacing and CRT leads (e.g., including a quadripolar connector or IS-1 type connector), and pacing leads with sensing capabilities (e.g., a pressure sensing/pacing lead with a quadripolar type connector). Other types of leads and/or lead connector types can also be used in conjunction with the implant tool 34, as desired.

Figure 2:
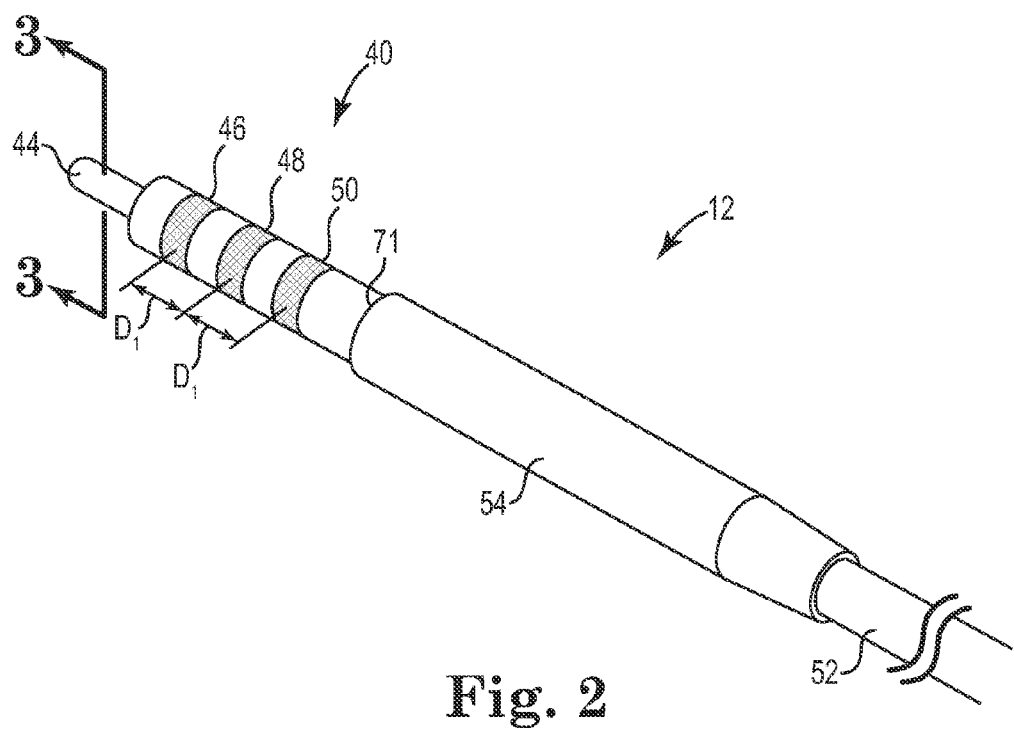
FIG. 2 is a perspective view showing the terminal end of the implantable lead of FIG. 1 in greater detail.

FIG. 2 is a perspective view showing the terminal end 40 of the implantable lead 12 of FIG. 1 in greater detail. As further shown in FIG. 2, the implantable lead 12 includes a lead terminal pin 44 and a number of terminal rings 46,48,50 each spaced axially apart from each other a distance $D_1$ along the length of the lead body 52. The terminal pin 44 is electrically coupled to the fixation helix 20 on the conductor end 16, and serves as a cathode for the implantable lead 12. In some embodiments, the cathode can also be a passive fixation electrode. The first terminal ring 46, in turn, is electrically coupled to the ring electrode 22, and serves as an anode for the implantable lead 12. The second terminal ring 48 is connected to a first shocking coil 24 that can be located in the right ventricle. The third terminal ring 50 is electrically coupled to a second shocking coil 24 that can be located in the superior vena cava, and can be utilized to provide shock therapy to the patient's heart 14. Various other configurations can also utilize a quadripolar connector such as that shown in FIG. 2, for example. In lieu of a ring electrode 22, in some embodiments, the shocking coil 24 in the right ventricle can serve the dual purpose of a rate/sense anode as well as a shocking coil for defibrillation. In this configuration, which is typical for an integrated bipolar lead, ring 46 and ring 48 can be connected together. Additionally, in some ICD leads that include a shocking coil in only the right ventricle 18, the terminal ring 50 would not be connected to a conductor.

Although the implantable lead 12 includes a terminal pin 44 and three terminal rings 46,48,50, in other embodiments the number and configuration of the terminal contacts may vary from that shown. In one embodiment, for example, the implantable lead 12 can comprise a bi-polar pacing lead including a single terminal pin and ring electrode. In other embodiments, the implantable lead 12 can comprise a CRT lead with four low-voltage electrodes. In one such embodiment, for example, the implantable lead 12 can comprise a VDD or single pass lead having two right ventricle (RV) electrodes and two right atrium (RA) electrodes. Other lead configurations are also possible.

Figure 3:
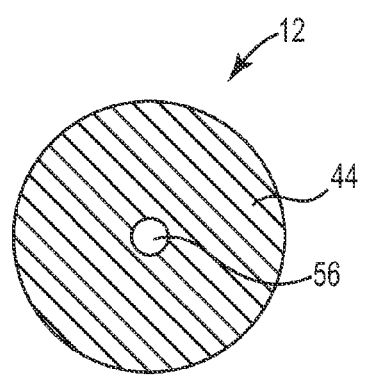
FIG. 3 is a transverse cross-sectional view showing the implantable lead across line 3-3 in FIG. 2.

FIG. 3 is a transverse cross-sectional view showing the implantable lead 12 across line 3-3 in FIG. 2. As further shown in FIG. 3, and in some embodiments, the lead body 52 has a circular cross-sectional shape, and includes an enlarged-diameter terminal boot 54 located distally of the terminal rings 46,48,50. In certain embodiments, the terminal pin 44 includes a pin lumen 56 sized and shaped to allow various stylets or guidewires to be inserted through the implantable lead 12 during the implantation procedure.

Figure 4:
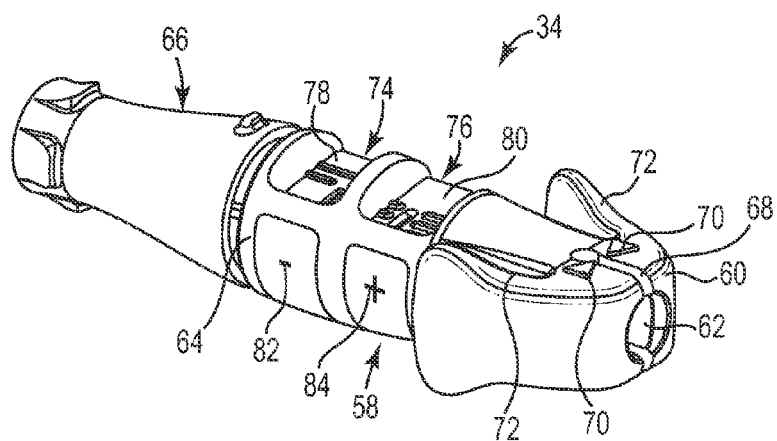
FIG. 4 is a perspective view showing a multi-function implant tool in accordance with an illustrative embodiment.

FIG. 4 is a perspective view showing a multi-function implant tool 34 in accordance with an illustrative embodiment. As shown in FIG. 4, the implant tool 34 includes a main body 58 having a distal clamping section 60 with an opening 62 that receives the terminal end 40 of the implantable lead 12, and a proximal section 64 operatively coupled to a knob mechanism 66 that can be used to rotatably engage or disengage the lead fixation helix 20 during lead implantation and testing. The distal section 60 of the main body 58 includes a slot 68 and a number of indicator arrows 70 that provide the implanting physician with visual feedback that the terminal end 40 of the implantable lead 12 is properly inserted into the implant tool 34. During insertion of the terminal end 40 into the opening 62, the indicator arrows 70 are configured to align with a proximal end 71 of the terminal boot 54 shown in FIG. 2. A number of levers 72 can be pushed together by the implanting physician to increase the diameter of the opening 62 slightly, allowing the terminal end 40 of the lead 12 to easily pass through the opening 62 and into the interior of the implant tool 34. When engaged, the levers 72 provide a clamping force on the implantable lead 12, which as discussed further herein, counteracts the engagement force used to drive the fixation helix 20 (e.g., and to slide a collet onto the terminal pin 44 for fixation helix 20 extension-retraction in the case of an active fixation lead) via the knob mechanism 66. The levers 72 also ensure that an adequate clamping force is applied to the terminal boot 54 regardless of the boot diameter.

In some embodiments, the shape of the implant tool 34 is configured such that the implanting physician can squeeze the device off of the lead while using the levers 72 to open the clamp. The shape of the levers 72 is configured such that the finger pressure required to squeeze the levers and open the clamp is relatively low. The area on the sides of the levers 72 is also shaped to facilitate gripping by the implanting physician. Other means for securing the lead 12 to the implant tool 34 can be utilized. In one alternative embodiment, for example, a ¼ turn cam lock or a push/pull cam lock can be used for securing the lead 12 to the implant tool 34.

Once the proper positioning of the implantable lead 12 within the implant tool 34 has been verified using the indicator arrows 70, the implanting physician then releases the levers 72, causing the size of the opening 62 to decrease slightly, thereby creating a friction fit between the main body 58 and the terminal end 40 of the lead 12. This friction fit between the main body 58 and the terminal end 40 of the implantable lead 12 is sufficient to prevent movement of the implant tool 34 during implantation of the lead 12 within the body, and to ensure that that the implant tool 34 stays in position during engagement of the knob mechanism 66 onto the terminal pin 44 when fixation helix 20 deployment or retraction is desired.

The main body 58 of the implant tool 34 further includes a number of side openings 74,76 each partially housing a respective electrical spring contact clip 78,80 used to electrically connect the conductors 42 of the Pacing System Analyzer (PSA) 38 to the terminal pin 44 and ring electrode 46 for testing. A number of polarity markings 82,84 disposed adjacent to each spring contact clip 78,80 are used to provide the implanting physician with information on which spring contact clip 78,80 correlates with the terminal pin 44 and ring contact 46. For example, a "−" marking on the side of the main body 58 adjacent to spring contact clip 78 provides the physician with visual feedback that the clip 78 is used to electrically connect the negative PSA conductor 42 to the terminal pin contact 44. Conversely, a "+" marking on the side of the main body 58 adjacent to spring contact clip 80 provides the implanting physician with visual feedback that the clip 80 is used to electrically connect the positive PSA conductor 42 to the ring contact 46.

Although only two side openings 74,76 and spring contact clips 78,80 are shown in FIG. 4, allowing the implanting physician to test the proper pacing function of the implantable lead 12, in other embodiments the implant tool 34 can include a greater or lesser number of electrical spring contact clips. In one alternative embodiment, for example, the implant tool 34 includes four side openings and four electrical spring contact clips electrically connected to the second and/or third ring contacts 48,50 to further permit testing of one or more shocking coil electrodes 24 in those embodiments in which the implantable lead 12 is configured for providing both pacing and defibrillation therapy. Additional electrical spring contact clips may also be provided for other types of multi-conductor leads. For an ICD lead, for example, a number of spring contact clips could be provided to check the impedance of the shocking coils. For a CRT lead, the additional spring contact clips could be used, for example, to check the impedance of additional pacing pathways within the heart.

Figure 5:
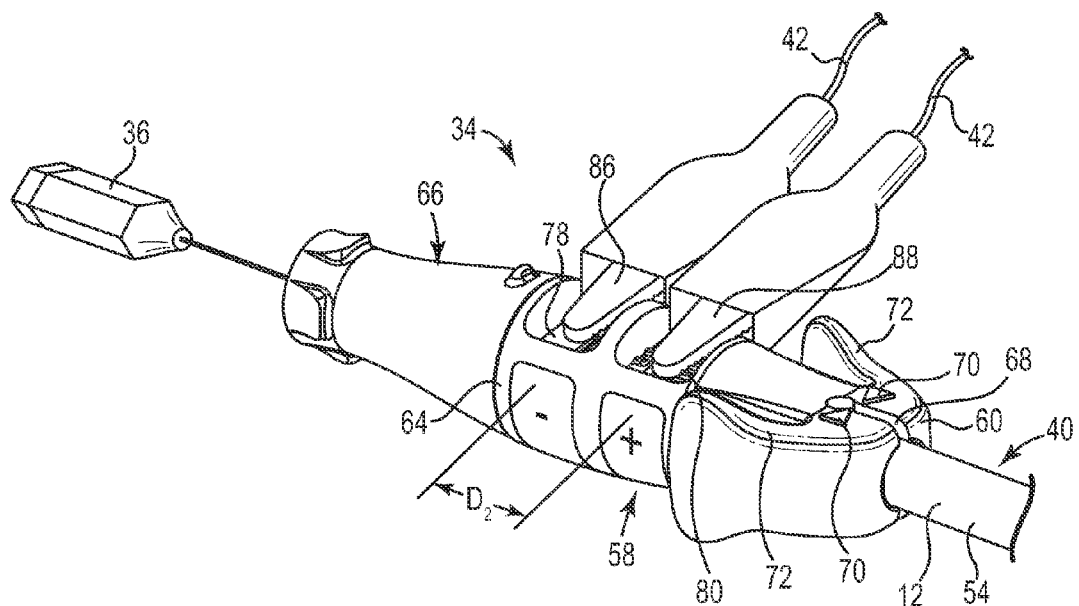
FIG. 5 is a perspective view showing the attachment of the implantable lead of FIG. 2, a stiffening member, and a number of electrical connection clips of a testing device connected to the multi-function implant tool of FIG. 4.

FIG. 5 is a perspective view showing the attachment of the implant tool 34 to the implantable lead 12, a stylet 36, and the conductors 42 of a Pacing System Analyzer (PSA) 38. As shown in FIG. 5, the electrical spring contact clips 78,80 are each configured to receive a corresponding alligator clip 86,88 on the end of each PSA conductor 42. In this fashion, the spring contact clips 78,80 form an interface between the alligator clips 86,88 and the terminal contacts 44,46 on the implantable lead 12, which serve to prevent the alligator clips 86,88 from directly engaging the surface of the contacts 44,46. In some embodiments, the spring contact clips 78,80 are spaced axially along the general length of the implant tool 34 such that the centerline distance $D_2$ between the alligator clips 86,88 is greater than the centerline distance between the terminal pin contact 44 and the first ring contact 46. This increase in axial spacing between the spring contact clips 78,80 along the length of the implant tool 34 facilitates attachment of the alligator clips 86,88 to the spring contact clips 78,80, and reduces the likelihood that the alligator clips 86,88 will come into contact with each other and short. The spring contact clips 78,80 also allow various types of PSA conductors 42 to be attached to the implant tool 34.

While the spring contact clips 78,80 are shown positioned adjacent to each other on one side of the implant tool 34, in other embodiments the spring contact clips 78,80 can be oriented at different angles from each other, allowing the alligator clips 86,88 to be inserted onto the spring contact clips 78,80 from different positions. In one embodiment, for example, the spring contact clips 78,80 can be oriented 180 degrees apart from each other such that the alligator clips 86,88 may be secured onto the clips 78,80 from opposite sides of the implant tool 34.

Figure 6A:
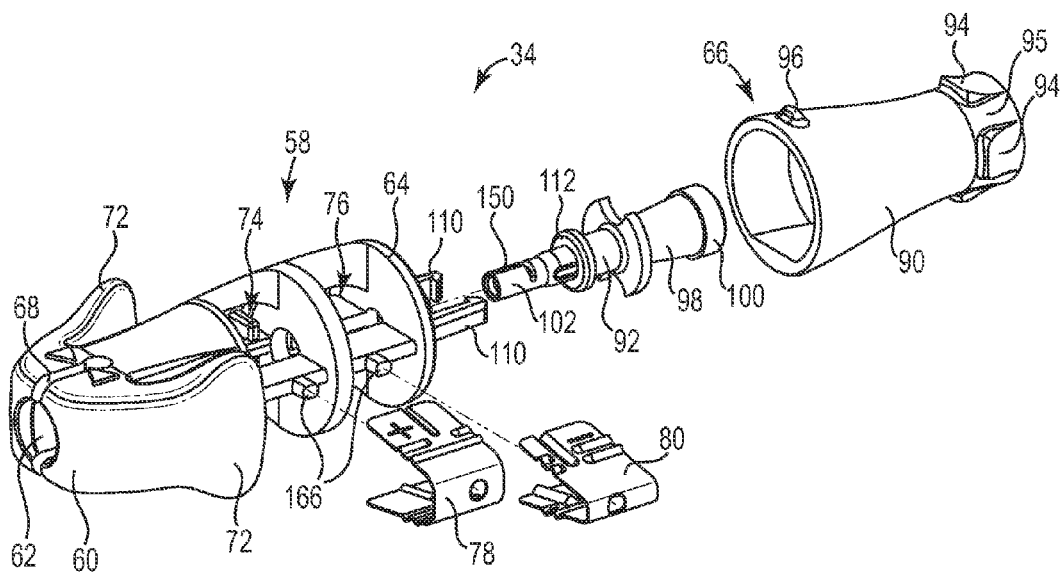
FIGS. 6A-6B are several assembly views showing the multi-function implant tool of FIG. 4 in greater detail.
Figure 6B:
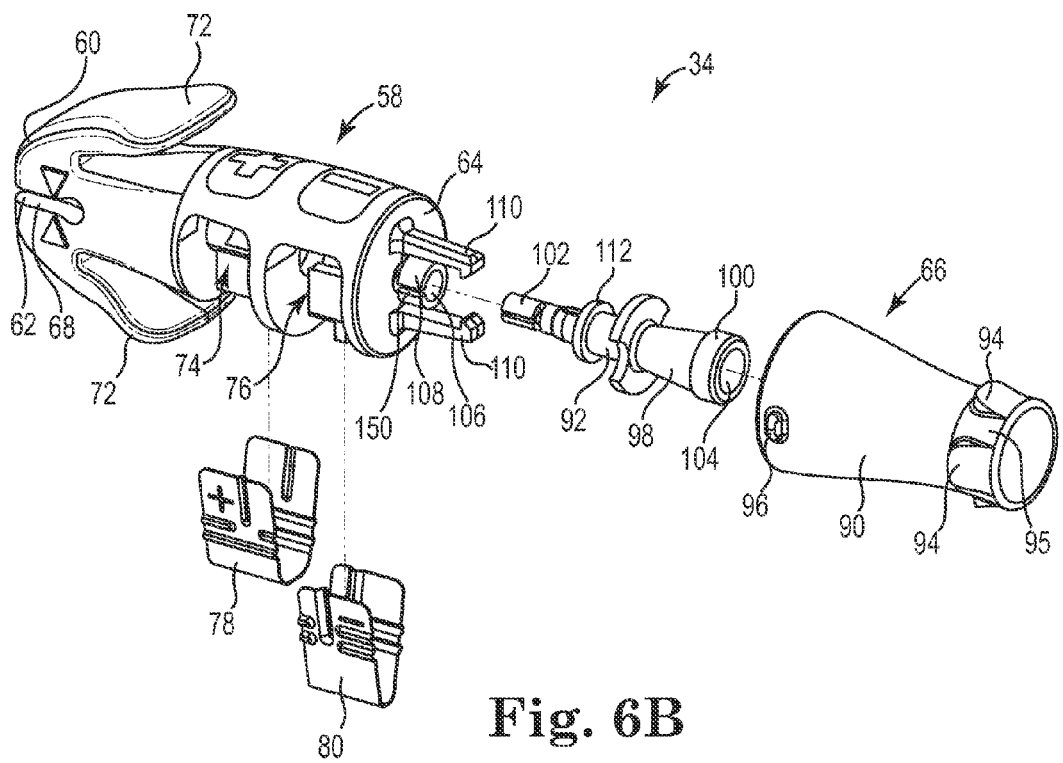

FIGS. 6A-6B are several assembly views showing the implant tool 34 in greater detail. As further shown in FIGS. 6A-6B, the knob mechanism 66 includes a knob 90 and a collet 92, which together are used to rotatably engage the terminal pin 44 to deploy the fixation helix 20 within the heart tissue. In those embodiments in which the implantable lead 12 is passively attached to the heart (e.g., via fixation tines), the knob mechanism 66 can be permanently locked, spun (e.g., to slip over the terminal pin), or omitted altogether.

When assembled together, the collet 92 is fixedly secured to the knob 90 such that rotation of the knob 90 in either a clockwise or counterclockwise direction results in a positive 1:1 rotation of the collet 92. The knob 90 is actuatable between a first, engaged position, which causes the collet 92 to engage the terminal pin 44, and a second, disengaged position, which causes the collet 92 to disengage from the terminal pin 44. In certain embodiments, for example, the knob 90 can be actuated to the engaged position for rotating the terminal pin 44 by pushing the knob 90 distally towards the main body 38. Conversely, the knob 90 can be actuated to the disengaged position by pulling the knob 90 proximally away from the main body 38. Since the implantable lead 12 is held stationary within the main body 58 of the implant tool 34, the fixation helix 20 can be actuated by rotating only the knob 90 instead of having to rotate the entire implant tool 34.

The knob 90 is sized and shaped to permit the implanting physician to rotate and pull the knob 90 proximally to disengage the collet 92. A number of finger grips 94 on one end of the knob 90 facilitate gripping of the knob 90 by the implanting physician. In some embodiments, the portion of the knob 90 at or near the finger grips 94 includes a crown 95, which further facilitates gripping of the knob 90. Other gripping features such as grooves or surface treatments can also be utilized to increase the grip. A counting nub 96 on the knob 90, in turn, may be used to count the number of knob rotations. In some cases, for example, the counting of the knob rotations can be used to provide the implanting physician with an estimate of when fixation helix deployment is expected. The counting nub 96 can be used to minimize x-ray exposures used in fluoroscopic visualization techniques for visualizing the fixation helix 20.

The collet 92 includes a collet body 98 having a first section 100 and a second section 102. The first section 100 is secured to an interior portion of the knob 90, and includes an opening 104 that allows the stylet 36 to pass through the collet 92 and into the pin lumen 56 of the implantable lead 12. The second section 102 of the collet 92 is sized and shaped to fit within an opening 106 of a clutch mechanism 108 that extends proximally from the proximal section 64 of the main body 58. A number of fingers 110 extending proximally from the main body 58 are configured to releasably engage a shoulder 112 on the collet body 98. During assembly, the fingers 110 are configured to engage the shoulder 112 when the second section 102 of the collet 92 is inserted into the opening 106 of the clutch mechanism 108.

Figure 7:
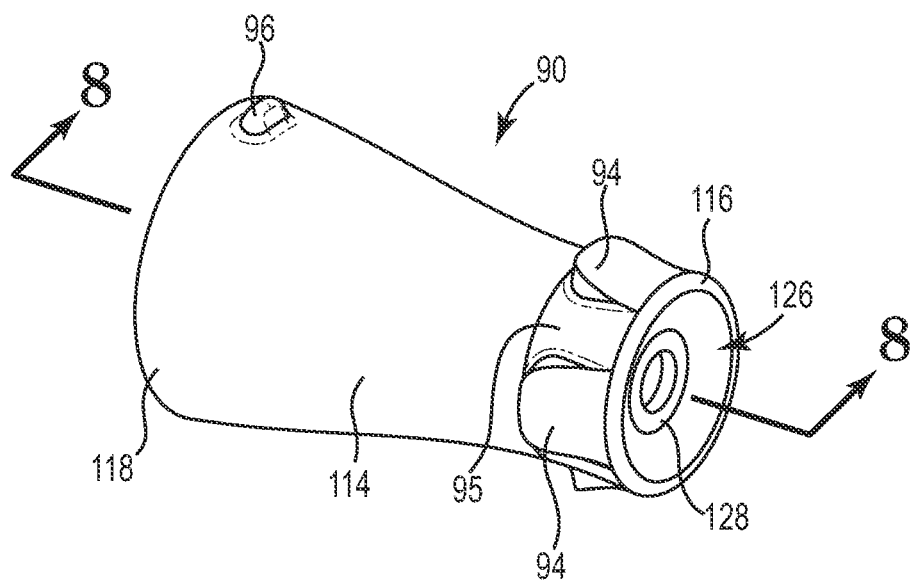
FIG. 7 is a perspective view showing the knob in greater detail.
Figure 8:
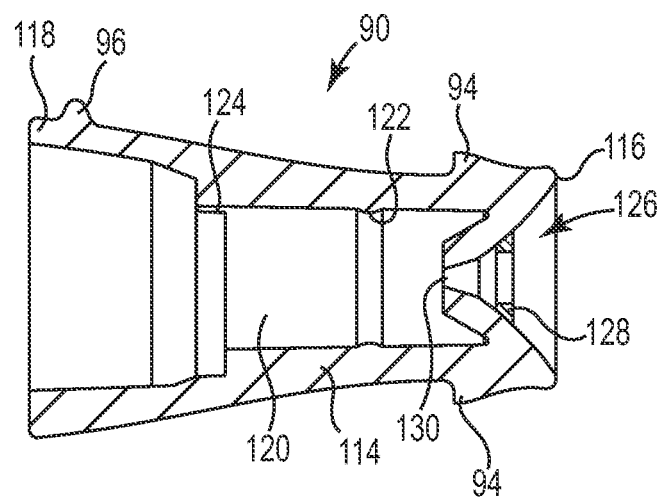
FIG. 8 is a longitudinal cross-sectional view showing the knob along line 8-8 in FIG. 7.

FIGS. 7-8 are several views showing the knob 90 in greater detail. As further shown in FIGS. 7-8, the knob 90 includes a knob body 114 having a proximal end 116 and a distal end 118. An interior portion 120 of the knob body 114 is configured to receive a portion of the collet 92, and further serves as a lumen through which various stylets 36 may pass through the collet 92 and into the pin lumen 56 of the implantable lead 12. The knob 90 is flared slightly along the length of the knob body 114 between the proximal and distal ends 116,118. A first projection 122 extending inwardly into the interior portion 120 of the knob body 114 is configured to engage a corresponding shoulder 134 (shown in FIG. 10) on the exterior of the collet 92, which serves to secure the collet 92 in place within the knob 90. A second number of projections 124 extending inwardly into the interior portion 120 of the knob body 114, in turn, are configured to engage a number of semi-circular fins 138,140 (shown in FIG. 9) on a portion of the collet 92. During rotation of the knob 90, these second projections 124 further secure the collet 92 in place within the knob 90. In other embodiments, the knob 90 and collet 92 comprise a single piece, thus obviating the need for the projections 124 and fins 138,140 to secure the two pieces together.

A flared opening 126 on the proximal end 116 of the knob 90 gradually tapers in diameter to facilitate insertion of the stylet 36 into the interior portion 120 of the knob 90, through the collet 92, and into the implantable lead 12. In some embodiments, and as further shown in FIGS. 7-8, the flared opening 126 further includes an annular-shaped wiper blade 128 located at or near a distal terminus 130 of the opening 126. A lubrication device comprises an absorbent material such as foam, foam rubber, or polystyrene, and is capable of storing an amount of mineral oil or other suitable lubricant. During insertion of the stylet 36 into the opening 126, the location of the wiper blade 128 and lubrication device adjacent to the distal terminus 130 causes the stylet 36 to come into contact with the wiper blade 128 and lubrication device. This contact serves to remove blood, body tissue, and other debris that may have been deposited on the stylet 36, and also lubricates the stylet 36 for easier insertion through the implant tool 34 and implantable lead 12.

Figure 9:
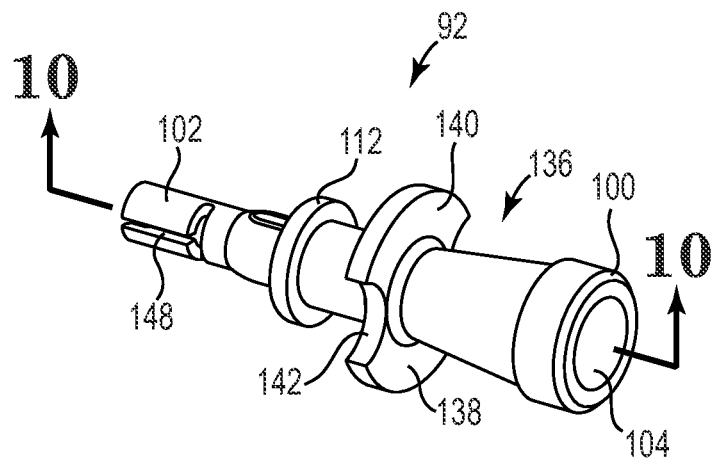
FIG. 9 is a perspective view showing the collet in greater detail.
Figure 10:
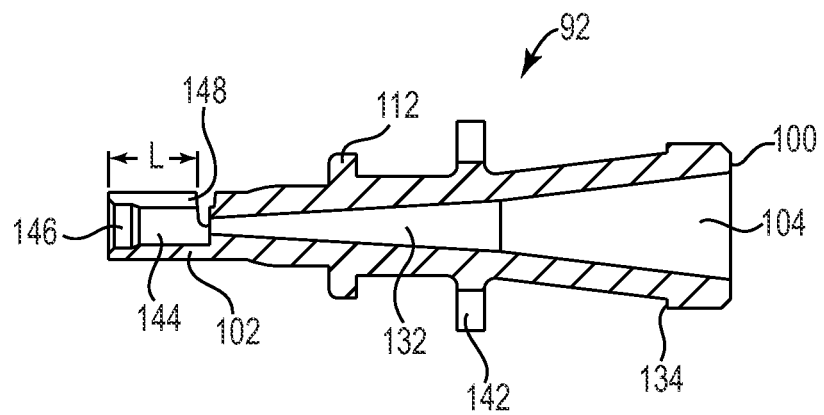
FIG. 10 is a longitudinal cross-sectional view showing the collet along line 10-10 in FIG. 9.

FIGS. 9-10 are several views showing the collet 92 in greater detail. As further shown in FIGS. 9-10, the collet body 98 is substantially conical-shaped, and includes an interior lumen 132 that gradually tapers along the length of the body 98 between the first section 100 and the second section 102. In use, this gradual tapering facilitates insertion of the stylet 36 through the opening 104 and through the lumen 132 towards the terminal pin lumen 56. A first shoulder 134 protruding outwardly from the exterior of the collet body 98 is configured to engage the first projection of the knob body 114 when the collet 92 is inserted into the knob 90 during assembly, securing the first section 100 of the collet 92 to the knob 90. A second shoulder 136, in turn, includes a number of semi-circular fins 138,140 extending outwardly from the exterior of the collet body 98, each of which are configured to rotatably engage the second projections 124 within the interior of the knob 90. Each of the second projections 124 within the knob interior 120 are configured to fit within an associated semi-circular cut-out 142 located between each semi-circular fin 138,140. During rotation of the knob 90, the second projections 124 on the knob 90 engage the semi-circular fins 138,140 on the collet 92, causing the collet 92 to rotate in like fashion.

A gripping sleeve 144 located on the second section 102 of the collet 92 is sized and shaped to frictionally receive the terminal pin 44 when the knob mechanism 66 is actuated to its engaged position. In some embodiments, the sleeve 144 has a length L similar to the length of the terminal pin 44, and has an inner diameter slightly smaller than the outer diameter of the pin 44 to provide a friction-fit between the terminal pin 44 and the collet 92 when the fixation knob 90 is actuated in the engaged position. The interior diameter of the collet 92 overlaps slightly with the terminal pin 44, even when the knob 90 is disengaged so that the stylet 36 easily passes through the collet 92 and terminal pin lumen 56 event when the knob 90 is disengaged.

One or more slits 148 located along the length L of the sleeve 144 permit the sleeve 144 to expand slightly when the terminal pin 44 is inserted into the sleeve 144, which occurs when the collet 92 is engaged. One or more slits 150 (see FIGS. 6A-6B) along the length of the clutch mechanism 108 similarly permit the member 108 to expand when the terminal pin 44 is inserted into the sleeve 144. A distal opening 146 of the sleeve 144 is flared slightly, increasing the diameter of the sleeve 144 at the distal-most end of the collet 92. This flared distal opening 146 ensures the collet 92 remains aligned to the terminal pin 44 when the fixation knob 90 is actuated to the disengaged position, causing the collet 92 to move proximally and disengage from the diametrical interference fit with the terminal pin 44. The difference in diameter between the sleeve 144 and the distal opening 146 thus acts as a clutch mechanism to secure the terminal pin 44 tightly within the sleeve 144. Other mechanisms for engaging the terminal pin 44 are also possible. In one alternative embodiment, for example, a ratchet mechanism could be used to engage/disengage the collet 92 from the terminal pin 44.

In some embodiments, the clutch mechanism functions as a self-braking mechanism to reduce recoil or slippage of the terminal pin 44 within the interior of the implant tool 34 as the implanting physician removes their hand to re-grip the knob 90 during each knob rotation. During each rotation of the knob 90, the clutch mechanism increases the friction of the clutch mechanism 150 about the second section 102 of the collet 92. This increased friction is sufficient to prevent the collet 92 from reversing as the knob 90 is being rotated to engage the fixation helix 20. If such recoil occurs, the torque applied on the knob 90 may not fully transmit to the fixation helix 20, causing the implanting physician to conclude that the implantable lead 12 is defective.

Figure 11:
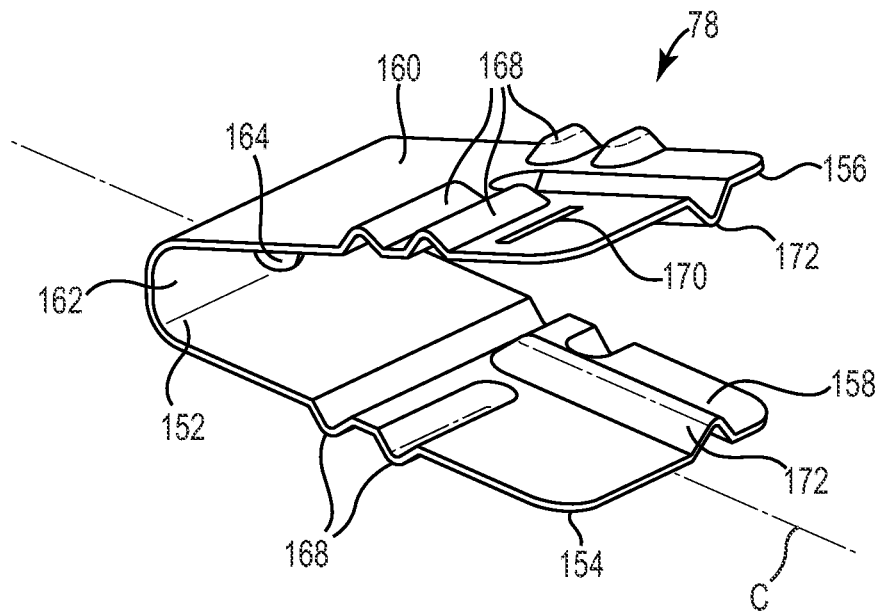
FIG. 11 is a perspective view showing an illustrative electrical spring contact clip adapted to mate with the terminal pin of an implantable lead inserted into the implant tool.

FIG. 11 is a perspective view showing an illustrative electrical spring contact clip 78 adapted to mate with the terminal pin 44 of an implantable lead 12 inserted into the implant tool 34. As shown in FIG. 11, the spring contact clip 78 comprises a U-shaped body 152 having a first end 154, a second end 156, an interior surface 158, and an exterior surface 160. The spring contact clip 78 is configured to bend or flex about a joint 162, causing the first and second ends 154,156 to move towards each other when an inwardly-directed force is applied to the exterior surface 160 from the alligator clip 86 of the PSA conductor 42. A stake hole 164 through the joint 162 is configured to receive a corresponding heat-set stake post 166 on the main body 58 of the implant tool 34, as shown, for example, in FIG. 6A. The spring contact clip 78 is secured within the side opening 76 of the main body 58 via the stake post 166 such that the ends 154,156 are free to move towards each other.

The spring contact clip 78 comprises an electrically conductive metal such as MP35N, nickel-plated steel, or nickel-plated beryllium copper, and functions as an intermediate electrical contact to facilitate the transfer of electrical signals back and forth between the PSA conductor 42 and the terminal pin 44. A number of external ridges 168 on the body 152 are configured to provide a gripping surface for alligator clip 86. A polarity marking 170 on one or both sides of the body 152 directs an implanting physician as to which alligator clip to attach to the spring contact clip 78.

A number of internal ridges 172 on the interior surface 158 of the spring contact body 152 are configured to engage the terminal pin 44 of the implantable lead 12 when the ends 154,156 are compressed together via the alligator clip 86, forming an electrical contact between the terminal pin 44 and the body 152. In some embodiments, the internal ridges 172 are laterally offset a distance from the centerline C of the spring contact body 152, which as discussed above with respect to FIG. 5, increases the axial separation distance $D_2$ between the alligator clips 86,88 by offsetting the centerline of the spring contact clip 78 relative to the adjacent clip 80. In other embodiments, the internal ridges 172 are located along the centerline C of the spring contact body 152, or are placed at other locations to adjust the separation distance $D_2$ between adjacent spring contact clips 78,80.

Figure 12:
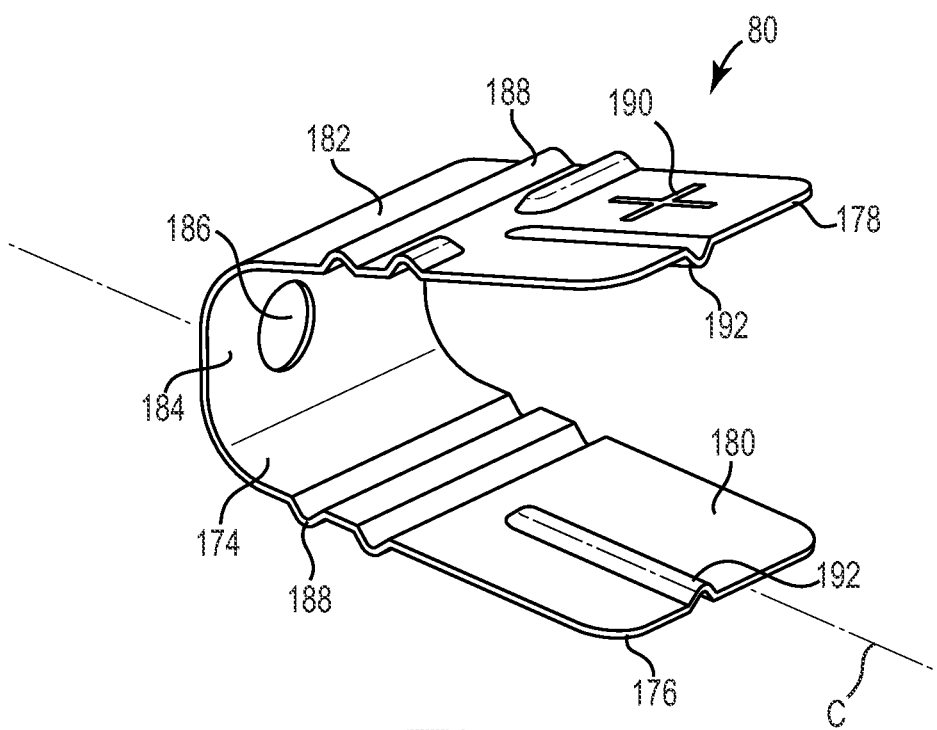
FIG. 12 is a perspective view showing an illustrative electrical spring contact clip adapted to mate with one of the ring contacts of an implantable lead inserted into the implant tool.

FIG. 12 is a perspective view showing an illustrative electrical spring contact clip 80 adapted to mate with the ring contact 46 of an implantable lead 12 inserted into the implant tool 34. The spring contact clip 80 comprises a U-shaped body 174 having a first end 176, a second end 178, an interior surface 180, and an exterior surface 182. The spring contact clip 80 is similarly configured to bend about a joint 184, causing the first and second ends 176,178 to move towards each other when an inwardly-directed force is applied to the exterior surface 182 from the alligator clip 88 of the PSA conductor 42. The separation of the first end 176 from the second end 178 is slightly greater than that of the spring contact body 152 that couples to the terminal pin contact 44 due to the increased diameter of the ring contact 46 relative to the pin 44. An opening 186 through the joint 184 is configured to receive a corresponding heat-set stake post 166 on the main body 58 of the implant tool 34 such that the ends 176,178 are free to move towards each other.

The spring contact clip 80 comprises an electrically conductive metal such as MP35N, nickel-plated steel, or nickel-plated beryllium copper, and functions as an intermediate electrical contact to facilitate the transfer of electrical signals back and forth between the PSA conductor 42 and the terminal ring contact 46. A number of external ridges 188 on the spring contact body 174 are configured to provide a gripping surface for the alligator clip 88. A polarity marking 190 on one or both sides of the body 174 directs an implanting physician as to which alligator clip to attach to the spring contact clip 80.

A number of internal ridges 192 on the interior surface 174 of the spring contact body 152 are configured to engage an associated ring contact 46 on the implantable lead 12 when the ends 176,178 are compressed together via the alligator clip 88, forming an electrical contact between the ring contact 46 and the body 174. In some embodiments, the internal ridges 192 are laterally offset a distance from the centerline C of the body 174. Alternatively, and in other embodiments, the internal ridges 192 are located along the centerline C, or are placed at other locations to adjust the separation distance $D_2$ between adjacent spring contact clips 78,80.

Figure 13:
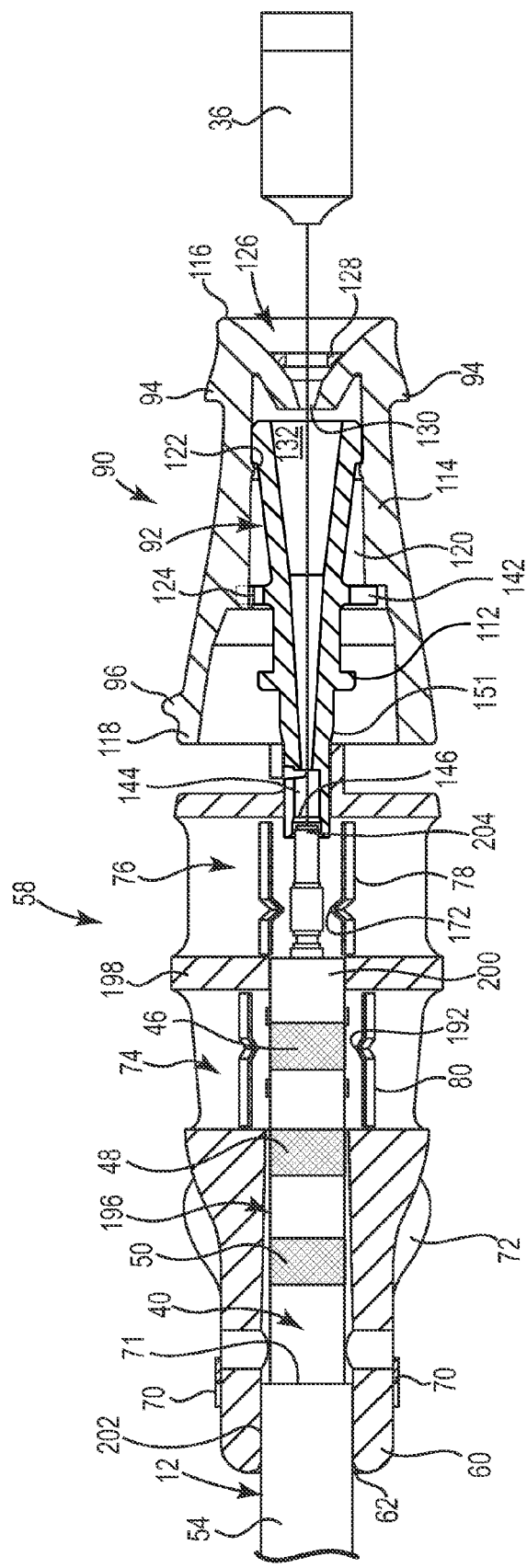
FIGS. 13-15 are several longitudinal cross-sectional views showing an illustrative method of using the implant tool of FIG. 4 to implant and test an implantable lead within the body.
Figure 14:
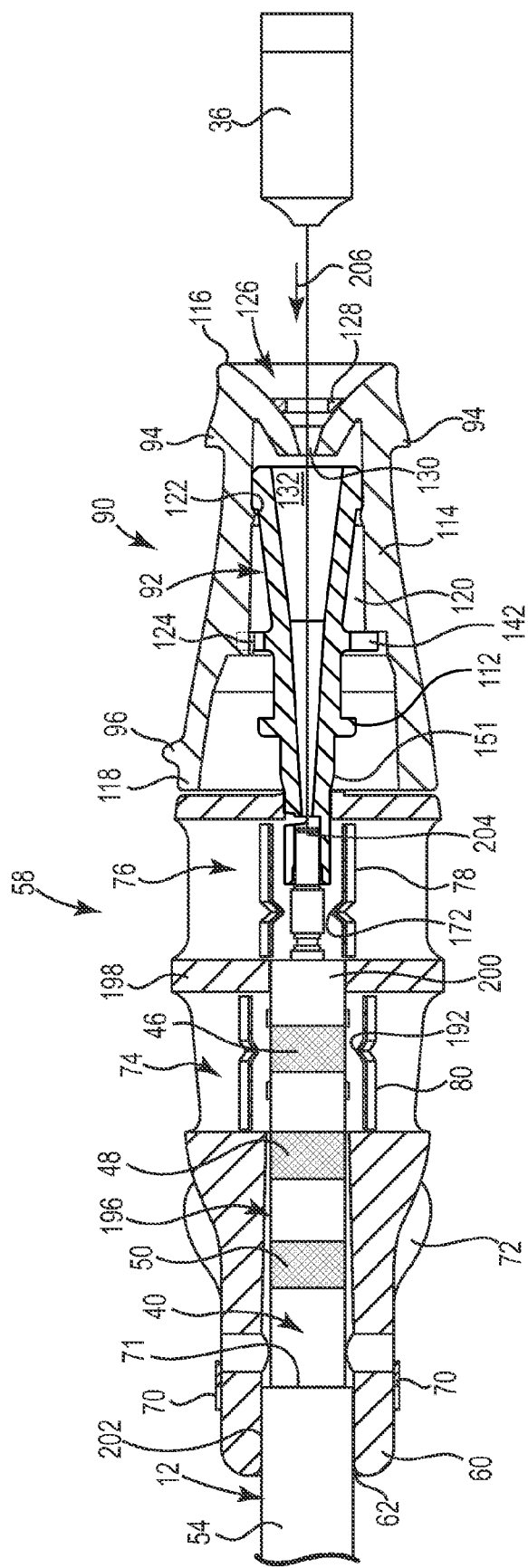
Figure 15:
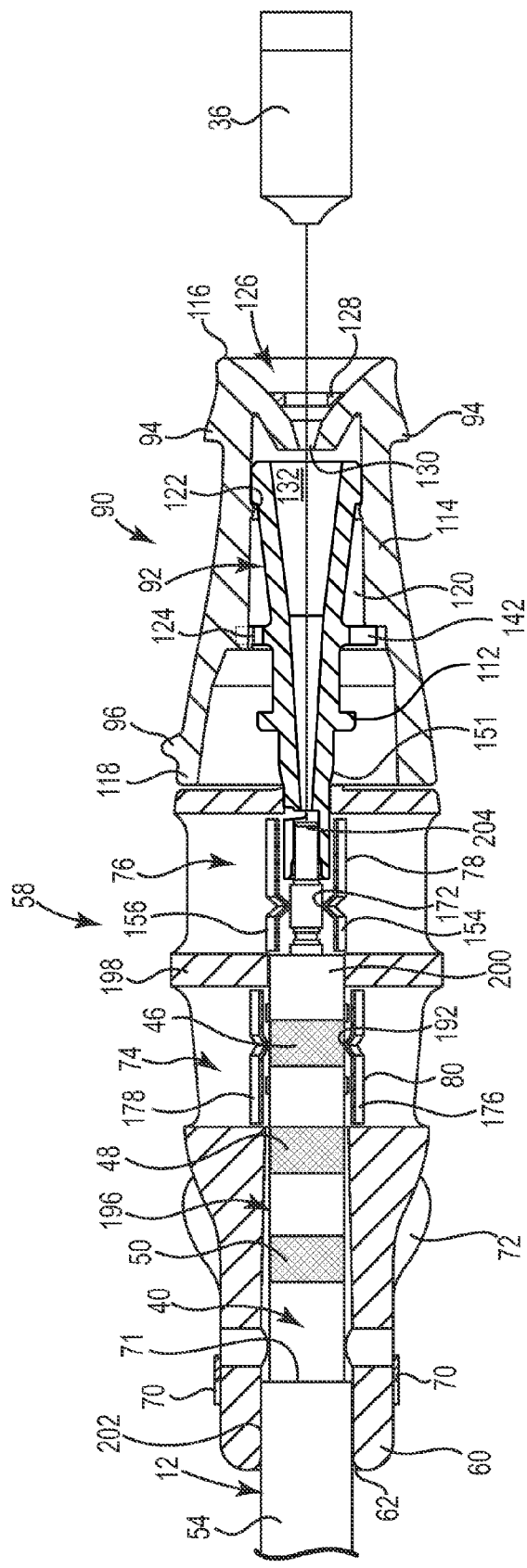

FIGS. 13-15 are several cross-sectional views showing an illustrative method of using the implant tool 34 to implant and test a lead 12 within the body. In preparation for implantation, the implanting physician may remove the implantable lead 12, implant tool 34, and stylet 36 from the device packaging, and push the terminal end 40 of the lead 12 into the opening 62 of the main body 58 while also pinching the levers 72 together. The distance at which the terminal end 40 is inserted through the opening 62 can be gauged using the slot 68 and indicator arrows 70. Once the proximal end 71 of the lead terminal boot 54 is aligned with the indicator arrows 70, the physician releases the levers 72, causing the distal section 60 of the main body 58 to crimp onto the proximal-most portion 71 of the lead terminal boot 54.

In the absence of the inwardly-directed force provided by the alligator clips 86,88, the electrical spring contact clips 78,80 are configured to expand outwardly to their equilibrium positions shown in FIGS. 11-12, creating a small gap or spacing between the internal ridges 172,192 and the pin and ring contacts 44,46. An interior lumen 196 of the main body 58 is also sized to form a gap around at least a portion of the terminal end 40 of the implantable lead 12. In some embodiments, and as further shown in FIGS. 13-15, the inner diameter of the interior lumen 196 gradually decreases in size along its length towards the proximal section 64 of the main body 58. A wall 198 forming part of the main body 58 separates the openings 74,76 from each other, and is configured to contact a proximal section 200 of the implantable lead 12, as shown. Due to the size and shape of the interior lumen 196, the terminal end 40 of the implantable lead 12 is supported at only sections 200 and 202 such that the terminal pin 44 and ring contacts 46,48,50 do not contact the main body 58 of the implant tool 34.

In a disengaged position shown in FIG. 13, the fixation knob 90 is pulled in a proximal direction, causing the collet 92 to disengage from the terminal pin 44. In this position, the proximal-most end 204 of the terminal pin 44 is located within only the distal opening 146. This aligns the collet 92 to the terminal pin 44 such that the pin 44 is held in position within the interior lumen 196 of the main body 58, but does not move in response to rotation of the knob 90.

To engage the terminal pin 44, and as further shown in FIG. 14, the implanting physician pushes the knob 90 distally towards the main body 58 in the direction indicated generally by arrow 206. Movement of the knob 90 towards the main body 58 causes the terminal pin 44 to enter the sleeve 144 within the collet 92. When this occurs, the sleeve 144 and clutch mechanism 108 are configured to frictionally engage the terminal pin 44. Once engaged, the implanting physician may then rotate the knob 90 in a counterclockwise direction to retract the fixation helix 20 from the implanting lead 12. In some embodiments, rotation of the knob 90 can be done manually, using the physicians fingers. Alternatively, and in other embodiments, a separate device such as a wrench could be used to rotate the knob 90 and engage the fixation helix 20. In one embodiment, for example, a wrench could be attached to a knob with an arm, finger hole, keyway, or other such feature. In another embodiment, the device comprises a molded part made from a soft polymeric material that stretches over the tip of the knob 90 and uses the crown 95 as a spline to turn the knob 90 and engage the fixation helix 20.

Continued rotation of the knob 90 in a clockwise direction causes the fixation helix 20 to enter the heart tissue. To gauge the insertion depth of the fixation helix 20 within the heart tissue, the implanting physician can count the number of knob turns using the counting nub 96 on the knob 90. The clutch mechanism 108 prevents the terminal pin 44 from recoiling or slipping during each successive turn of the knob 90. In some embodiments, the implant tool 34 is configured to produce a clicking sound during each rotation cycle, providing the physician with audible feedback that the fixation helix 20 is being rotated.

The fixation helix 20 is extended into heart tissue by rotating the terminal pin 44 via the knob 90. The terminal pin 44 is coupled to a driveshaft or a coil conductor serving as a driveshaft. The torque is typically applied in a clockwise direction in order to deploy the fixation helix 20 within the heart tissue. After helix deployment, it is often desirable to release the excess clockwise torque. If the excess torque is not released, then this may lead to an increase in turncount, leading the implanting physician to improperly conclude that the mechanism is malfunctioning.

To release any torque imparted to the implantable lead 12, the implanting physician pulls the knob 90 proximally back to the disengaged position shown in FIG. 13, causing the terminal pin 44 to disengage from within the sleeve 144 of the collet 92. This can be done, for example, after every application of a clockwise or counterclockwise torque in order to ensure consistent helix extension-retraction performance. In this position, the terminal pin 44 is free to rotate within the interior lumen 196 of the main body 58, relieving any torque imparted to the implantable lead 12 during engagement of the fixation helix 20 into the heart tissue. Once this torque is relieved, the implanting physician can then push the knob 90 distally back to the engaged position shown in FIG. 14.

To test the implantable lead 12 prior to attachment to an implantable device (e.g., a pulse generator), the implanting physician connects the alligator clips 86,88 to the electrical spring contact clips 78,80, as shown, for example, in FIG. 5. As can be further seen in FIG. 15 with the alligator clips 86,88 hidden for purposes of illustration, the inwardly-directed spring force of the alligator clips 86,88 causes the ends 176, 178,154,156 of the electrical spring contact clips 78,80 to move toward each other which, in turn, causes the interior ridges 172,192 on the clips 78,80 to contact the corresponding terminal contact 44,46. With the alligator clips 86,88 connected to the spring contact clips 78,80, the implanting physician may then adjust the positioning of the implantable lead 12 and/or the fixation helix 20, as discussed above. Once this process is complete, the implanting physician can then remove the alligator clips 86,88 and stylet 36 from the implant tool 34. The implant tool 34 can then be removed from the implantable lead 12 by engaging the release levers 72 and pulling the terminal end 40 out through the opening 62. The terminal end 40 of the implantable lead 12 can then be connected to another device implanted within the body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implant tool for use with an implantable lead, the implant tool comprising:
   a main body having a distal clamping section, a proximal section, and an interior lumen, the distal clamping section including an opening adapted to frictionally receive a terminal boot of the implantable lead;
   a plurality of spring contact members coupled to the main body and exposed on an exterior of the implant tool; and
   a knob mechanism coupled to the main body, the knob mechanism slidably actuatable along a central axis of the implant tool between a first position configured to frictionally engage a terminal pin of the implantable lead and a second position configured to disengage the implant tool from the terminal pin to facilitate torque release, the knob mechanism connected to the main body in each of the first and second positions, the knob mechanism configured to rotate relative to the main body when in the first position to rotate the terminal pin relative to the terminal boot, the knob mechanism slidably actuatable between the first and second positions independent of relative rotation between the knob mechanism and the main body, wherein the knob mechanism slides along the central axis, farther away from the main body, when slidably actuated from the first position to the second position.

2. The implant tool of claim 1, wherein the main body further includes a number of levers configured to adjust the size of the opening for creating a friction-fit between the main body and the terminal boot of the implantable lead.

3. The implant tool of claim 1, wherein the distal clamping section of the main body includes a slot and a number of indicator arrows for confirming the positioning of the terminal boot within the implant tool.

4. The implant tool of claim 1, wherein the knob mechanism includes a collet coupled to a knob.

5. The implant tool of claim 4, wherein the knob includes a funneled opening configured for receiving a stiffening member.

6. The implant tool of claim 5, wherein the knob opening includes a wiper blade and a lubrication device.

7. The implant tool of claim 4, wherein the collet includes a collet body having a first section secured to an interior portion of the knob and a second section configured to engage a clutch mechanism of the main body.

8. The implant tool of claim 7, wherein the collet body includes a gripping sleeve configured to frictionally receive the terminal pin in said first position.

9. The implant tool of claim 7, wherein the collet body includes a flared distal opening configured to receive a proximal end of the terminal pin in said second position.

10. The implant tool of claim 7, wherein the knob mechanism further includes a self-braking mechanism configured for eliminating recoil of the knob during rotation of the knob mechanism.

11. The implant tool of claim 1, wherein each spring contact member includes a clip having an exterior facing surface configured to receive an electrical connector and an interior facing surface configured to engage an electrical contact on the terminal boot of the implantable lead.

12. The implant tool of claim 1, wherein the plurality of spring contact members are aligned laterally from each other along a length of the implant tool.

13. The implant tool of claim 1, wherein the plurality of spring contact members includes:
   a first spring contact clip configured to engage the terminal pin of the implantable lead; and
   a second spring contact clip configured to engage a ring contact of the implantable lead.

14. The implant tool of claim 13, further comprising at least one additional spring contact clip configured to engage a contact of the implantable lead.

15. The implant tool of claim 1, wherein each spring contact member includes a body having a first end bendable relative to a second end.

16. The system of claim 1, wherein the implantable lead further comprises a fixation helix that is extendable from the implantable lead by relative rotation between the terminal boot and the terminal pin of the implantable lead, and wherein the distal clamping section is configured to hold the terminal boot stationary while rotation of the knob mechanism is configured to rotate the terminal pin to extend the fixation helix from the implantable lead while the terminal boot remains stationary.

17. A system for implanting and testing an implantable lead within the body of a patient, the system comprising:
   an implantable lead comprising a terminal pin, a terminal boot, and a fixation helix that is extendable from the implantable lead by relative rotation between the terminal boot and the terminal pin; and
   an implant tool comprising:
      a main body having a distal clamping section, a proximal section, and an interior lumen, the distal clamping section including an opening adapted to frictionally receive the terminal boot of the implantable lead;
      a plurality of spring contact members coupled to the main body; and
      a knob mechanism coupled to the main body, the knob mechanism slidably actuatable along a central axis of the implant tool between a first position configured to frictionally engage a terminal pin of the implantable lead and a second position configured to disengage from the terminal pin, wherein the knob mechanism slides along the central axis, farther away from the main body, when slidably actuated from the first position to the second position,
      wherein the knob mechanism is configured to rotate the terminal pin relative to the terminal boot, while the terminal boot is held by the distal clamping section and while the knob mechanism is in the first position, to extend the fixation helix from the implantable lead.

18. The implant tool of claim 17, wherein an inner profile of the interior lumen of the main body is adjustable by a user control to create a friction-fit between the main body and the terminal boot of the implantable lead.

19. The implant tool of claim 17, wherein the knob mechanism includes a collet coupled to a knob, the collet including a collet body having a first section secured to an interior portion of the knob and a second section configured to engage a clutch mechanism of the main body.

* * * * *